United States Patent
Joshi

(10) Patent No.: US 6,602,523 B1
(45) Date of Patent: Aug. 5, 2003

(54) COMPOSITE MATERIAL AND PROCESS FOR INCREASING BIOAVAILABILITY AND ACTIVITY OF A BENEFICIAL AGENT

(75) Inventor: Ashok V. Joshi, Salt Lake City, UT (US)

(73) Assignee: Technology Holding, LLC., Salt Lake City, UT (US)

( * ) Notice: Subject to any disclaimer, the term of this patent is extended or adjusted under 35 U.S.C. 154(b) by 0 days.

(21) Appl. No.: 09/641,120

(22) Filed: Aug. 17, 2000

(51) Int. Cl.$^7$ ................................................ A61K 9/14
(52) U.S. Cl. ...................... 424/489; 424/400; 424/493; 424/464; 424/466
(58) Field of Search ................... 424/466, 489, 424/493, 400

(56) References Cited

U.S. PATENT DOCUMENTS

| | | | |
|---|---|---|---|
| 3,923,969 A | * 12/1975 | Baukal et al. | 424/468 |
| 4,344,934 A | 8/1982 | Martin et al. | 424/80 |
| 4,517,179 A | 5/1985 | Raghunathan | 514/249 |
| 5,164,186 A | * 11/1992 | Tsuru et al. | 424/422 |
| 5,407,458 A | * 4/1995 | Konig et al. | 420/427 |
| 5,460,831 A | * 10/1995 | Kossovsky et al. | 424/493 |
| 5,641,515 A | 6/1997 | Ramtoola | 424/189 |
| 5,879,716 A | * 3/1999 | Katz et al. | 424/501 |
| 5,922,299 A | * 7/1999 | Bruinsma et al. | 423/335 |
| 6,087,353 A | * 7/2000 | Stewart et al. | 514/182 |
| 6,344,271 B1 | * 2/2002 | Yadav et al. | 428/402 |
| 6,350,470 B1 | * 2/2002 | Pather et al. | 424/466 |

* cited by examiner

Primary Examiner—Thurman K. Page
Assistant Examiner—Robert M. Joynes
(74) Attorney, Agent, or Firm—Jody L. Factor

(57) ABSTRACT

A composite material suitable for external and/or internal association with a living body comprising: a first component having a surface area greater than approximately 10 $M^2/gm$; and a first beneficial agent associated with at least a portion of the high surface area of the first component, wherein the first component is fabricated from a material having a hardness greater than the hardness of the first beneficial agent.

15 Claims, 2 Drawing Sheets

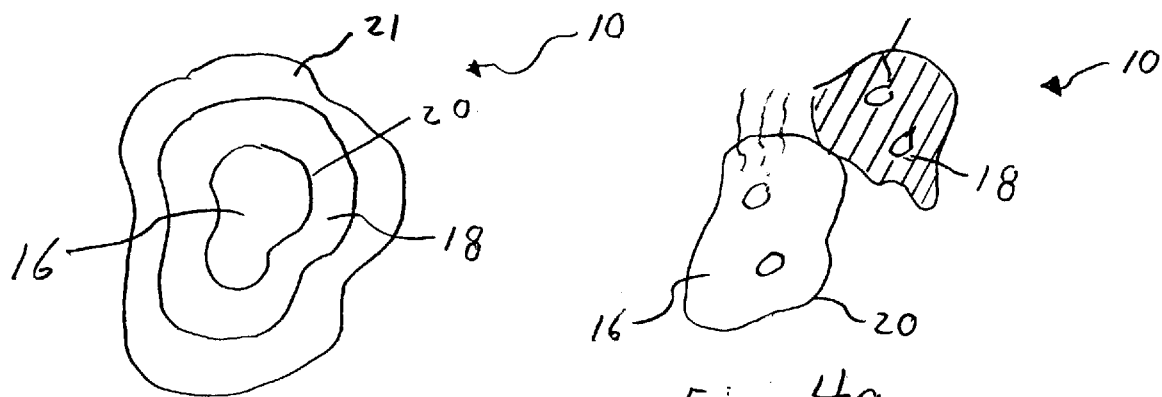
Fig. 4c
Fig. 4a
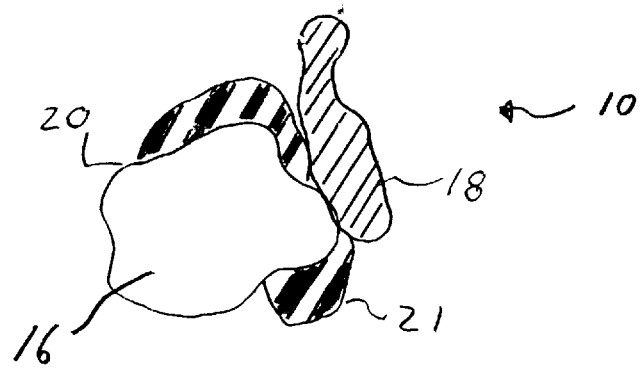
Fig 4b
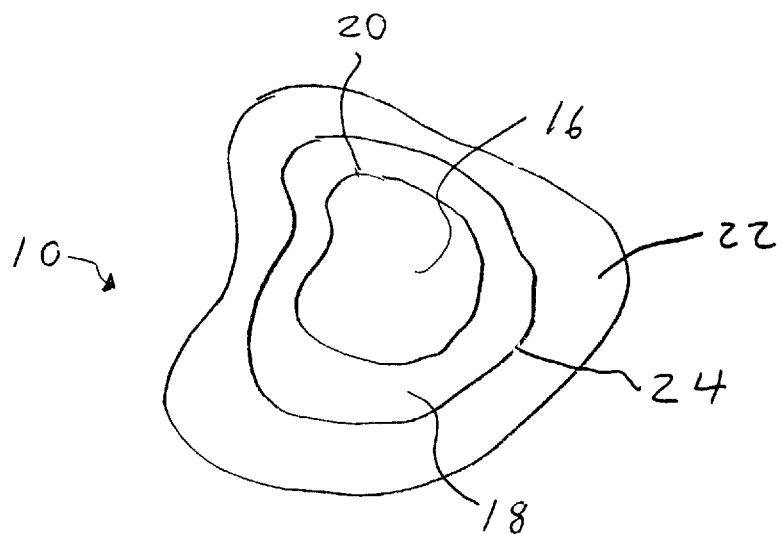
Fig 5

COMPOSITE MATERIAL AND PROCESS FOR INCREASING BIOAVAILABILITY AND ACTIVITY OF A BENEFICIAL AGENT

BACKGROUND OF THE INVENTION

1. Field of the Invention

The present invention relates in general to a composite material, and more particularly, to a composite material having a beneficial agent associated with another high surface area component. Such a composite material enables increased bioavailability and/or activity of the beneficial agent, and can be used in numerous applications, including topical, oral and/or systemic administration of a medicament, pharmaceutical agent, chemical agent, etc.

2. Background Art

Beneficial agents have been known in the art for years and are the subject of numerous patents, including U.S. Pat. No. 4,344,934, U.S. Pat. No. 4,517,179, and U.S. Pat. No. 5,641,515.

U.S. Pat. No. 4,344,934 discloses medical compositions comprising wetted mixtures of poorly soluble drugs with water soluble polymers which are useful in increasing bioavailability of associated drugs.

U.S. Pat. No. 4,517,179 discloses rapidly dissolving uniform compositions of low water solubility drugs formed from a dry mixture of the drug having a reduced particle size in combination with properly selected and sized excipients including microcrystalline cellulose, dibasic calcium phosphate, starches and a lubricant.

U.S. Pat. No. 5,641,515 discloses a controlled release pharmaceutical formulation comprising nanoparticles formed of a biodegradable polycyanoacrylate polymer in which insulin is entrapped.

While beneficial agents have become common in numerous applications, the efficiency of their administration remains problematic for several applications. In particular, numerous beneficial agents comprise molecules which are undesirably insoluble in an associated environment to the extent that they are not sufficiently bioavailable during a predetermined administration period. One way to increase the solubility of the beneficial agent is by configuring the beneficial agent into nanoparticles. However, in doing so these agents commonly aggregate, conglomerate, and/or coagulate. Upon aggregation, conglomeration, and/or coagulation, the effective surface area of the beneficial agent can be dramatically decreased. As a result, the beneficial agent is not effectively soluble, and, in turn, truly bioavailable, due to decreased surface area of the beneficial agent.

It is therefore an object of the present invention to associate a beneficial agent with a high surface area inert component or another high surface area beneficial agent to substantially maintain a predetermined effective high surface area of the beneficial agent to that of the high surface area inert component. When such an effective high surface area is maintained, the bioavailability and activity of the beneficial agent can be improved substantially.

These and other objects of the present invention will become apparent in light of the present specification, claims, and drawings.

SUMMARY OF THE INVENTION

The present invention is directed to a composite material suitable for external and/or internal association with a living body comprising: (1) a first component having a surface area greater than 10 $M^2/gm$; and (2) a first beneficial agent associated with at least a portion of the surface of the first component.

In a preferred embodiment of the invention, the first component is fabricated from a material having an hardness greater than the hardness of the first beneficial agent.

Preferably, the first component comprises: (1) a diameter ranging from approximately 1 to approximately 100 nanometers; and (2) a substantially inert material. It is also contemplated that the inert first component be fabricated from either a hygroscopic or hydrated material.

In another preferred embodiment of the invention, the first component is fabricated from at least one material selected from the group consisting essentially of noble metals such as Ag, Pt, Rh, Au, etc., metal oxides, metal nitrides, metal carbides, metal phosphates, carbonaceous materials, ceramic materials, and mixtures thereof.

In yet another preferred embodiment of the invention, the first component is fabricated from at least one material selected from the group consisting essentially of zeolites, $Ag_2O$, Ag, Au, $Ta_2O_5$, $Al_2O_3$, $TiO_2$, C, $SiO_2$, $Bi_2O_3$, ZnO and mixtures and compounds thereof. In such an embodiment, the first component may be fabricated from an antibacterial material. In an alternative embodiment of the present invention, the first component could be fabricated from hydrated ceramic materials.

In accordance with the present invention, the first beneficial agent is fabricated from at least one material selected from the group consisting essentially of a pharmaceutical agent, a medicament, a chemical agent, and mixtures thereof. The first beneficial agent may also be associated with an effervescent material.

Additionally, a second beneficial agent may be processed such that the composite is formed between the second beneficial agent and the first beneficial agent. In this embodiment, the first beneficial agent may be fabricated from a material having a hardness and surface area greater than the hardness and surface area of the second beneficial agent.

The present invention is also directed to a composite material suitable for external and/or internal association with a living body comprising: (1) a first beneficial agent having a high surface area; and (2) a second beneficial agent associated with at least a portion of the surface of the first beneficial agent.

In a preferred embodiment of the invention, a tertiary beneficial agent may also be associated with at least a portion of the surface of the second beneficial agent.

The present invention is also directed to a process for fabricating a composite material comprising the steps of: (1) providing a first component having a high surface area; (2) providing a first beneficial agent; and (3) associating the first beneficial agent with at least a portion of the surface of the first component.

The present invention is further directed to a process for fabricating a composite material, comprising the steps of: (1) providing a first beneficial agent having a surface area greater than 10 $M^2/gm$; (2) providing a second beneficial agent; and (3) associating the second beneficial agent with at least a portion of the surface of the first beneficial agent.

DESCRIPTION OF THE DRAWINGS

The invention will now be described with reference to the drawings wherein:

FIGS. 4a, 4b and 4c of the drawings are schematic representations of a fourth embodiment of a composite material fabricated in accordance with the present invention; and FIG. 5 of the drawings is a schematic representation of a fifth embodiment of a composite material fabricated in accordance with the present invention.

DETAILED DESCRIPTION OF THE INVENTION

Figure 1A:
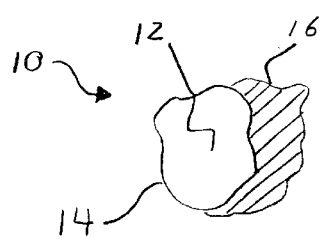
FIGS. 1a and 1b of the drawings are schematic representations of a first embodiment of a composite material fabricated in accordance with the present invention.

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

It will be understood that like or analogous elements and/or components, referred to herein, are identified throughout the drawings by like reference characters.

Figure 1B:
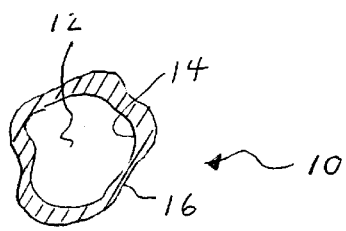

Referring now to the drawings and to FIG. 1a and 1b in particular, composite material 10 is shown in a first embodiment as generally comprising first component 12 having a surface 14, and first beneficial agent 16 associated with at least a portion of surface 14 of the first component 12. As will be discussed in greater detail below, first component 12 and first beneficial agent 16 of composite material 10 are fabricated from materials suitable for external and/or internal association with a living body, such as a human, cow, horse, dog, bird, fish, etc. As such, it is desirous to maintain a high effective surface area of the first beneficial agent so as to maximize its administration efficiency and minimize administration cost and/or toxicity.

First component 12 is preferably fabricated from a material having a hardness greater than the hardness of first beneficial agent 16. It will be understood that when the hardness of first component 12 is greater than the hardness of first beneficial agent 16, the first beneficial agent will, upon association with surface 14 of first component 12, substantially increase its effective surface area, and in turn, its bioavailability and/or activity.

While the effective surface area of first component 12 may vary depending upon the conditions of intended use, it will be understood that a preferred effective surface area of greater than approximately 10 $M^2$/gm is desirous for most applications. First component 12 may vary in diameter from approximately 1 to approximately 100 nanometers, and more preferably from approximately 1 to approximately 50 nanometers.

As previously discussed, first component 12 is fabricated from a material suitable for internal and/or external association with a living body. As such, first component 12, is preferably, substantially inert with respect to a living body. Examples of suitable materials include, noble metals (e.g. Ag, Pt, Rh, Au, etc.), metal oxides (e.g. $Ag_2O$, Ag, Au, $Ta_2O_5$, $Al_2O_3$, $TiO_2$, $Bi_2O_3$, ZnO, $CaCO_3$, MgPO4 etc.), metal nitrides, metal carbides, carbonaceous materials, ceramic materials, zeolites and mixtures thereof are especially useful in applications where it is desirous for the first component to exhibit antibacterial properties.

First beneficial agent 16 is fabricated from a material which is capable of performing a material benefit to a living body. Examples of such materials include, a pharmaceutical agent, a medicament, a chemical agent, and mixtures thereof.

Figure 2A:
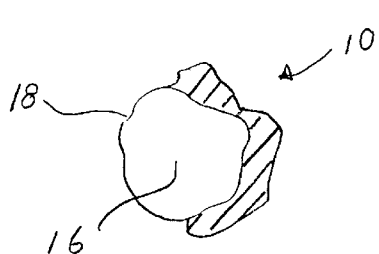
FIGS. 2a and 2b of the drawings are schematic representations of a second embodiment of a composite material fabricated in accordance with the present invention.
Figure 2B:
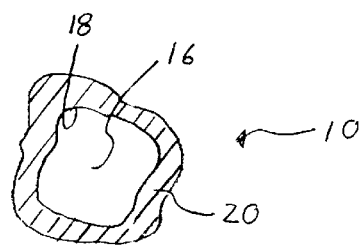

As is best shown in FIGS. 2a and 2b, composite material 10 may also include second beneficial agent 18, which can be applied to at least a portion of surface 20 of first beneficial agent 16. In this embodiment, it is desirous for first beneficial agent 16 to be fabricated from a material having a hardness greater than the hardness of second beneficial agent 18. It will be understood that when composite material 10 comprises multiple beneficial agents, the beneficial agents may function independently of each other, or alternatively, may function together to, for example, generate a derivative species within/with on the living body.

Figure 3A:
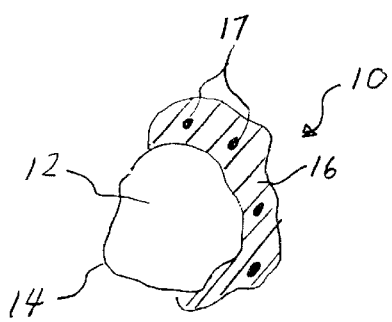
FIGS. 3a, 3b and 3c of the drawings are schematic representations of a third embodiment of a composite material fabricated in accordance with the present invention.
Figure 3B:
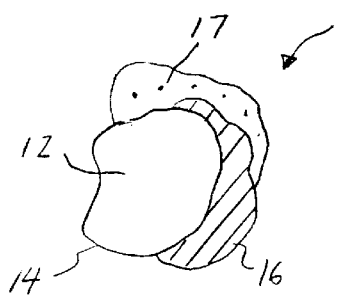
Figure 3C:
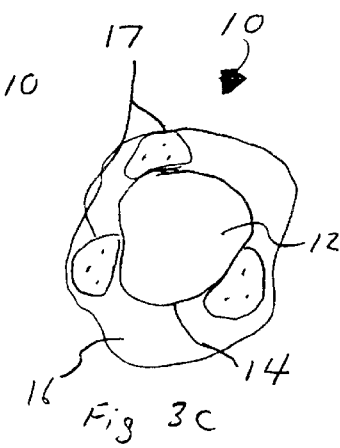

In a third embodiment of the present invention, and as is best shown in FIGS. 3a, 3b and 3c, first beneficial agent 16 can be associated with effervescent material 17. Effervescent material 17 serves to further increase the bioavailability and/or activity of first beneficial agent 16 upon placement in, for example, an aqueous medium. It will be understood that. the composition and availability of numerous effervescent materials is well known in the art.

Referring now to FIGS. 4a, 4b and 4c, composite material 10 is shown as comprising first beneficial agent 16 having surface 20, and second beneficial agent 18 associated with at least a portion of surface 20 of first beneficial agent 16. Similar to the above-provided embodiments, it is desirous for first beneficial agent 16 to be fabricated from a material having a hardness greater than the hardness of second beneficial agent 18. Although not shown, it is also contemplated that one or both of first and second beneficial agents 16 and 18, respectively, can be associated with an effervescent material 21.

As is shown in FIG. 5, tertiary beneficial agent 22 can be associated with at least a portion of surface 24 of second beneficial agent 18.

The present invention is also directed to a process for fabricating a composite material as disclosed herein. In first and second steps of the process, a first component having a surface area greater than 10 $M^2$/gm and a beneficial agent are provided. Once provided, the beneficial agent is associated with at least a portion of the high surface area of the first component. Such association may be occur via any one of a number of conventional methods, including, spraying, brushing, rolling, dip coating, powder coating, misting, and/or chemical vapor depositing the beneficial agent to at least a portion of the high surface area of the first component. Although not necessary, the primary beneficial agent and/or the first component can be milled to a predetermined dimension prior to or after association with each other.

An alterative composite material can be fabricated in accordance with the present invention upon providing a first beneficial agent having a high surface area, and a second beneficial agent. After the above-identified materials have been provided, the second beneficial agent can be associated with at least a portion of the high surface area of the first beneficial agent.

It will be understood that composite materials in accordance with the present invention can be administered externally or internally to a living body for numerous applications, wherein one or more beneficial agents maintain a predetermined effective surface area as a result of being associated with the surface of a small particle having a hardness greater than the hardness of the beneficial agent(s).

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A composite material suitable for external and/or internal association with a living body and for rapid release of a beneficial agent, comprising:

particles consisting essentially of a core component and at least one beneficial agent;

the core component having a surface area greater than approximately 10 $M^2/gm$, wherein the core component is a stoichiometrically stable material, said core component is an inorganic material selected from the group consisting of noble metals, metal oxides, metal nitrides, metal carbides, metal phosphates, metal carbonates, metal sulfates, metal halides, carbonaceous materials, ceramic materials, zeolites, $SiO_2$ and mixtures thereof;

the beneficial agent is adsorbed on at least a portion of the surface of the core component; and wherein the core component is fabricated from a material having a hardness greater than the hardness of the first beneficial agent to, in turn, increase bioavailability of the first beneficial agent.

2. The composite material according to claim 1, wherein the beneficial agent is associated with an effervescent material.

3. The composite material according to claim 1, wherein the core component comprises a diameter ranging from approximately 1 to 100 nanometers.

4. The composite material according to claim 1 wherein the core component comprises either hygroscopic or hydrated material.

5. The composite material according to claim 1, wherein the core component is fabricated from at least one material selected from the group consisting essentially of, $Al_2O_3$, $TiO_2$, C, Ag, Au, $Ag_2O$, and mixtures thereof.

6. The composite material according to claim 1, wherein the core component is fabricated from an antibacterial material.

7. The composite material according to claim 1, wherein the beneficial agent is fabricated from at least one material selected from the group consisting essentially of a pharmaceutical agent, a medicament, a chemical agent, and mixtures thereof.

8. The composite material according to claim 1, wherein the beneficial agent comprises a first and a second beneficial agent wherein the second beneficial agent is associated with at least a portion of the first beneficial agent.

9. The composite material according to claim 8, wherein the first beneficial agent is fabricated from a material having an hardness greater than the hardness of the second beneficial agent.

10. A composite material suitable for external and/or internal association with a living body and for rapid release of a beneficial agent, comprising:

particles consisting essentially of a core component and at least one beneficial agent;

the core component having a surface area greater than approximately 10 $M^2/gm$, wherein the core component is a stoichiometrically stable material, said core component is an inorganic material selected from the group consisting of noble metals, metal oxides, metal nitrides, metal carbides, metal phosphates, metal carbonates, metal sulfates, metal halides, carbonaceous materials, ceramic materials, zeolites, $SiO_2$ and mixtures thereof;

the beneficial agent is adsorbed on at least a portion of the surface of the core component;

wherein the core component is fabricated from a material having a hardness greater than the hardness of the beneficial agent adsorbed thereon; and wherein the core component serves to increase the effective surface area of the beneficial agent relative to a beneficial agent unassociated with a core component, and, in turn, to increase bioavailability of the beneficial agent.

11. A process for fabricating a composite material for rapid release of a beneficial agent, comprising the steps of:

providing particles consisting essentially of a core component and at least one beneficial agent wherein the core component has a hardness and a surface area greater than approximately 10 $M^2/gm$, and wherein the core component is a stoichiometrically stable material, wherein said core component is an inorganic material selected from the group consisting of noble metals, metal oxides, metal nitrides, metal carbides, metal phosphates, metal carbonates, metal sulfates, metal halides, carbonaceous materials, ceramic materials, zeolites, $SiO_2$ and mixtures thereof;

the beneficial agent has a hardness less than the hardness of the core component to, in turn increase bioavailability of the beneficial agent; and adsorbing the beneficial agent on at least a portion of the surface of the core component.

12. The process according to claim 11, further comprising the step of milling the beneficial agent and the core component.

13. The process according to claim 11, wherein the step of absorbing comprises spraying, brushing, rolling, dip coating, powder coating, misting, and/or chemical and/or physical vapor depositing the beneficial agent on at least a portion of the surface of the core component.

14. The process according to claim 11 wherein the beneficial agent comprises a first beneficial agent and a second beneficial agent, the process further comprising the step of:

associating the second beneficial agent with at least a portion of the first beneficial agent.

15. A process for increasing the exposed surface area of a beneficial agent and for rapid release of a beneficial agent comprising the steps of:

providing particles consisting essentially of a core component and at least one beneficial agent wherein the core component has a hardness and a surface area greater than approximately 10 $M^2/gm$, wherein the core component is a stoichiometrically stable material, wherein said core component is an inorganic material selected from the group consisting of noble metals, metal oxides, metal nitrides, metal carbides, metal phosphates, metal carbonates, metal sulfates, metal halides, carbonaceous materials, ceramic materials, zeolites, $SiO_2$ and mixtures thereof;

the beneficial agent has a hardness less than the hardness of the and adsorbing the beneficial agent on at least a portion of the surface of the core component, and in turn, increasing the surface area of the beneficial agent relative to the surface of the core component to, in turn, increase bioavailability of the beneficial agent.

* * * * *